(12) United States Patent
Culhane

(10) Patent No.: US 8,496,570 B2
(45) Date of Patent: *Jul. 30, 2013

(54) BONE GROWTH STIMULATOR

(75) Inventor: Jeffrey James Culhane, San Marcos, CA (US)

(73) Assignee: DJO, LLC, Vista, CA (US)

( * ) Notice: Subject to any disclaimer, the term of this patent is extended or adjusted under 35 U.S.C. 154(b) by 547 days.

This patent is subject to a terminal disclaimer.

(21) Appl. No.: 12/270,708

(22) Filed: Nov. 13, 2008

(65) Prior Publication Data

US 2009/0163761 A1 Jun. 25, 2009

Related U.S. Application Data

(63) Continuation of application No. 11/188,943, filed on Jul. 25, 2005, now Pat. No. 7,465,269, which is a continuation-in-part of application No. 29/234,200, filed on Jul. 14, 2005, now Pat. No. Des. 544,604.

(51) Int. Cl.
*A61N 2/00* (2006.01)

(52) U.S. Cl.
USPC .......................................................... 600/13

(58) Field of Classification Search
USPC .......................................... 600/9–15; 607/51
See application file for complete search history.

(56) References Cited

U.S. PATENT DOCUMENTS

| | | | |
|---|---|---|---|
| 946,193 A | 1/1910 | Bachelet | |
| 2,102,790 A | 12/1937 | Drollinger | |
| 2,172,998 A | 9/1939 | Grout et al. | |
| D164,558 S | 9/1951 | Kasley | |
| D237,344 S | 10/1975 | Whitten | |
| 4,066,065 A | 1/1978 | Kraus | |
| 4,266,533 A | 5/1981 | Ryaby et al. | |
| D279,642 S | 7/1985 | Ross | |
| 4,550,714 A | 11/1985 | Talish et al. | |
| 4,757,804 A | 7/1988 | Griffith et al. | |
| 4,818,697 A | 4/1989 | Liboff et al. | |
| 4,932,951 A | 6/1990 | Liboff et al. | |
| 5,059,298 A | 10/1991 | Liboff | |
| 5,067,940 A | 11/1991 | Liboff et al. | |
| 5,078,674 A | 1/1992 | Cadwell | |
| 5,087,336 A | 2/1992 | Liboff et al. | |
| 5,088,976 A | 2/1992 | Liboff et al. | |
| 5,099,756 A | 3/1992 | Franconi et al. | |
| 5,100,373 A | 3/1992 | Liboff et al. | |
| 5,106,361 A | 4/1992 | Liboff et al. | |

(Continued)

FOREIGN PATENT DOCUMENTS

| | | |
|---|---|---|
| CA | 1314941 | 3/1993 |
| EP | 0 104 793 | 4/1984 |
| WO | WO-2005/056111 | 6/2005 |

OTHER PUBLICATIONS

Printed brochure describing External PEMP Fields: Application of Spinal-Stim Lite, manufactured by Orthofix; 1990.

*Primary Examiner* — Christine Matthews
(74) *Attorney, Agent, or Firm* — Ropes & Gray LLP

(57) ABSTRACT

A bone growth stimulator is provided. In one embodiment, the device has an elliptically shaped transducer coil. The coil provides increased therapeutic benefit to a wearer. An elliptically shaped housing supports and contains the coil. The housing includes a curvature when viewed in profile, such that a first surface of the housing is convex. The convex surface is adapted to be positioned against a wearer's lower back, to nest within the natural curvature thereof.

12 Claims, 6 Drawing Sheets

U.S. PATENT DOCUMENTS

| | | | |
|---|---|---|---|
| 5,123,898 | A | 6/1992 | Liboff et al. |
| 5,131,904 | A | 7/1992 | Markoll |
| 5,139,474 | A | 8/1992 | Lamond et al. |
| 5,143,588 | A | 9/1992 | Liboff et al. |
| 5,160,591 | A | 11/1992 | Liboff et al. |
| 5,195,940 | A | 3/1993 | Baylink |
| 5,215,633 | A | 6/1993 | Liboff et al. |
| 5,215,642 | A | 6/1993 | Liboff et al. |
| 5,267,939 | A | 12/1993 | Liboff et al. |
| 5,269,745 | A | 12/1993 | Liboff et al. |
| 5,290,409 | A | 3/1994 | Liboff et al. |
| D345,799 | S | 4/1994 | Lamond et al. |
| 5,312,534 | A | 5/1994 | Liboff et al. |
| 5,318,561 | A | 6/1994 | McLeod et al. |
| 5,330,410 | A | 7/1994 | Baylink |
| 5,401,233 | A | 3/1995 | Erickson et al. |
| 5,415,617 | A | 5/1995 | Kraus |
| 5,458,558 | A | 10/1995 | Liboff et al. |
| 5,518,495 | A | 5/1996 | Kolt |
| 5,518,496 | A | 5/1996 | McLeod et al. |
| D384,160 | S | 9/1997 | Kusnets et al. |
| 5,792,040 | A | 8/1998 | Koeneman et al. |
| 5,817,000 | A | 10/1998 | Souder |
| 5,842,966 | A | 12/1998 | Markoll |
| D411,303 | S | 6/1999 | Scagliotti |
| 6,007,476 | A | 12/1999 | Wascher et al. |
| D427,319 | S | 6/2000 | Chen |
| 6,083,149 | A | 7/2000 | Wascher et al. |
| 6,149,577 | A | 11/2000 | Bouldin et al. |
| D435,661 | S | 12/2000 | Chen |
| 6,179,770 | B1 | 1/2001 | Mould |
| 6,186,941 | B1 | 2/2001 | Blackwell |
| 6,371,958 | B1 | 4/2002 | Overaker |
| 6,418,345 | B1 * | 7/2002 | Tepper et al. .................. 607/51 |
| D463,560 | S | 9/2002 | Michelson |
| D496,377 | S | 9/2004 | Pinchot |
| 2004/0176805 | A1 | 9/2004 | Whelan et al. |
| 2005/0228462 | A1 | 10/2005 | Brighton et al. |

* cited by examiner

BONE GROWTH STIMULATOR

CROSS-REFERENCE TO RELATED APPLICATION

This application is a continuation of application Ser. No. 11/188,943, filed Jul. 25, 2005, the entire contents of which are hereby expressly incorporated by reference, which is a continuation-in-part of application Ser. No. 29/234,200, titled: BONE GROWTH STIMULATOR, filed on Jul. 14, 2005, the entire contents of which are hereby expressly incorporated by reference.

BACKGROUND OF THE INVENTION

1. Field of the Invention

The present invention relates to devices for stimulating the growth of bone cells.

2. Description of the Related Art

Magnetic field therapy is often used to treat a variety of medical conditions. For example, the following U.S. patents teach various devices and methods of applying magnetic fields to treatment sites: U.S. Pat. No. 4,818,697 to Liboff et al., issued Apr. 4, 1989, titled "Techniques for Enhancing the Permeability of Ions Through Membranes;" U.S. Pat. No. 4,932,951 to Liboff et al., issued Jun. 12, 1990, titled "Method and Apparatus for Controlling Tissue Growth and an Applied Fluctuating Magnetic Field;" U.S. Pat. No. 5,059,298 to Liboff, issued Oct. 22, 1991, titled "Method and Apparatus for Regulating Transmembrane Ion Movement;" U.S. Pat. No. 5,195,940 to Baylink, issued Mar. 23, 1993, titled "Method for Increased Production of Growth Factor in Living Tissue Using an Applied Fluctuating Magnetic Field;" U.S. Pat. No. 5,330,410 to Baylink, issued Jul. 19, 1994, titled "Method for Increased Production of Growth Factor in Living Tissue Using an Applied Fluctuating Magnetic Field;" and U.S. Pat. No. 5,792,040 to Koeneman et al., issued Aug. 11, 1998, titled "Patient Interface Device for Generating Therapeutic Magnetic Fields." Each of the above-listed patents is assigned to the assignee of the present application, and each is incorporated herein by reference in its entirety.

To apply a magnetic field to a treatment site, various wearer interface devices have been designed that place one or more magnetic field generating coils adjacent a body region that is to be treated. U.S. Pat. No. 5,139,474, entitled, "Medical Treatment Device with Self-Centering Securing Members," illustrates one example of such a wearer interface device. The apparatus described therein engages a region of a wearer's body, such as a limb, with a pair of coils in opposed relation relative to the treatment region. This prior art apparatus has a relatively rigid shell comprising two rigid shell halves that are hinged together at a single hinge axis. The two shell halves pivot away from each other to a non-treating position and pivot towards each other in a treatment position. Means are provided for securing the shell halves together in the treatment position. One coil is disposed in each shell half and the pair of coils are used to generate the therapeutic magnetic field. That is, a voltage of a given amplitude and frequency is applied to the coils to induce a current and produce a magnetic field. Resilient securing members extend inward from the shell halves and have a flexible backing that applies a force radially from the shell halves. The resilient securing members deform outward to conform to the anatomy of the region to which it is applied.

U.S. Pat. No. 4,616,629, entitled "Coil Construction for Electromagnetic Treatment of an Afflicted Body Region," describes a single-coil wearer interface device defining two U-shaped cavities. The two cavities are of unequal size, which permits the device to fit two different sizes of anatomical structures. Canadian Patent No. 1,314,941 discloses a treatment coil that is generally circular, having outwardly spiraling multiple strands of conductors.

SUMMARY OF THE INVENTION

The preferred embodiments of the present bone growth stimulator have several features, no single one of which is solely responsible for their desirable attributes. Without limiting the scope of this bone growth stimulator as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include increased therapeutic benefit, and an ergonomic design that is comfortable for wear against the wearer's lower back.

One embodiment of the present bone growth stimulator comprises a transducer coil adapted to receive a voltage input and generate a magnetic field output, and a housing adapted to support and contain the transducer coil. The housing includes a curvature when viewed in profile, such that a first side of the housing is convex.

Another embodiment of the present bone growth stimulator comprises a transducer coil adapted to receive a voltage input and generate a magnetic field output, and a housing adapted to support and contain the transducer coil. The housing has an elliptical shape, and is adapted to be positioned against a wearer's lower back such that a major axis and a minor axis of the elliptical housing are substantially perpendicular to the anterior/posterior axis.

Another embodiment of the present bone growth stimulator comprises a method of stimulating bone growth. The method comprises the steps of positioning a transducer coil in the lumbar region of a wearer's back, and applying a voltage across the coil to produce a magnetic field around the coil. The coil has an elliptical shape, and is positioned against the wearer's back such that a major axis and a minor axis of the elliptical coil are substantially perpendicular to the wearer's anterior/posterior axis.

BRIEF DESCRIPTION OF THE DRAWINGS

The preferred embodiments of the present bone growth stimulator, illustrating its features, will now be discussed in detail. These embodiments depict the novel and non-obvious bone growth stimulator shown in the accompanying drawings, which are for illustrative purposes only. These drawings include the following figures, in which like numerals indicate like parts.

DETAILED DESCRIPTION OF THE PREFERRED EMBODIMENTS

Figure 1:
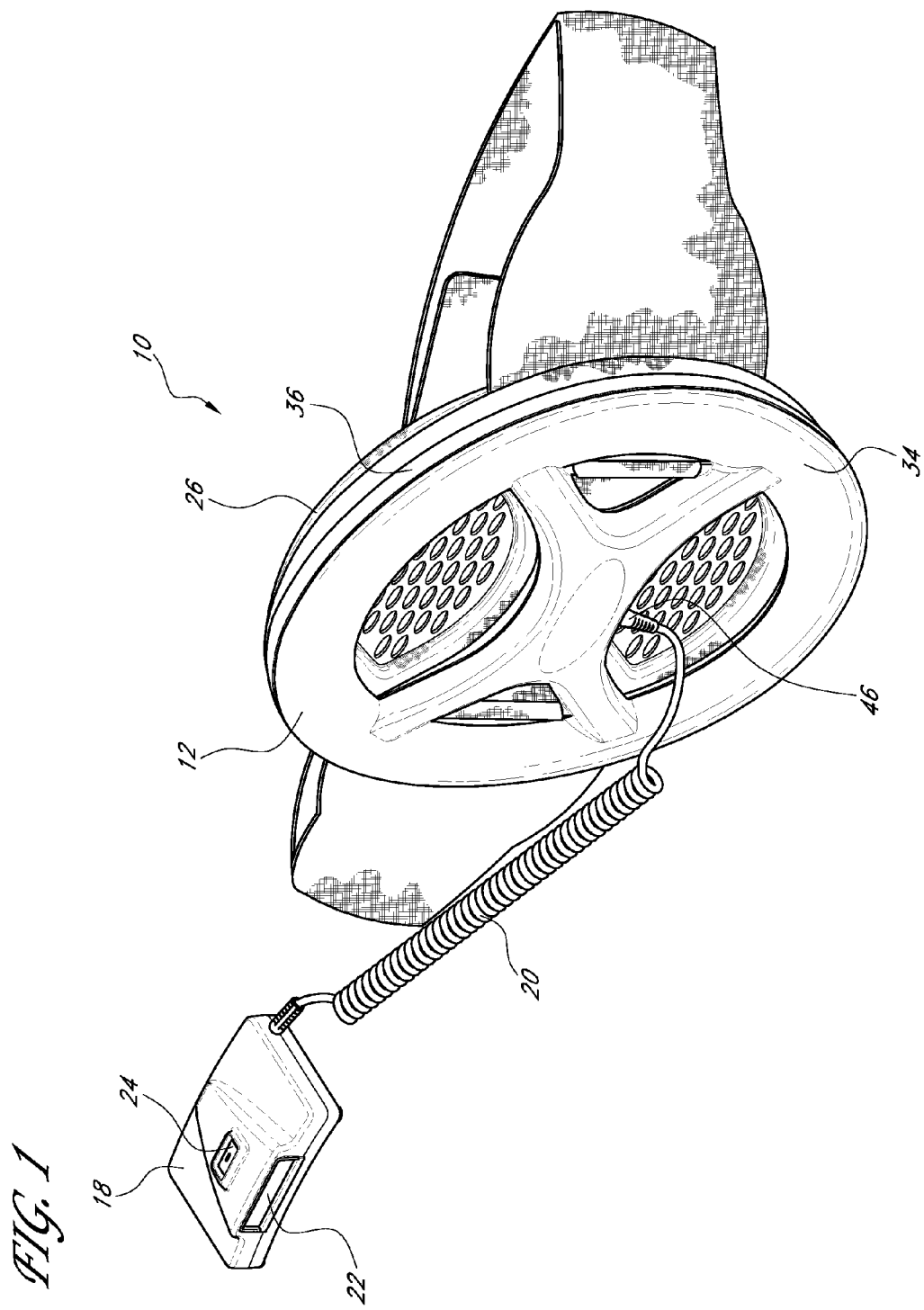
FIG. 1 is a front perspective view of a preferred embodiment of the present bone growth stimulator.
Figure 2:
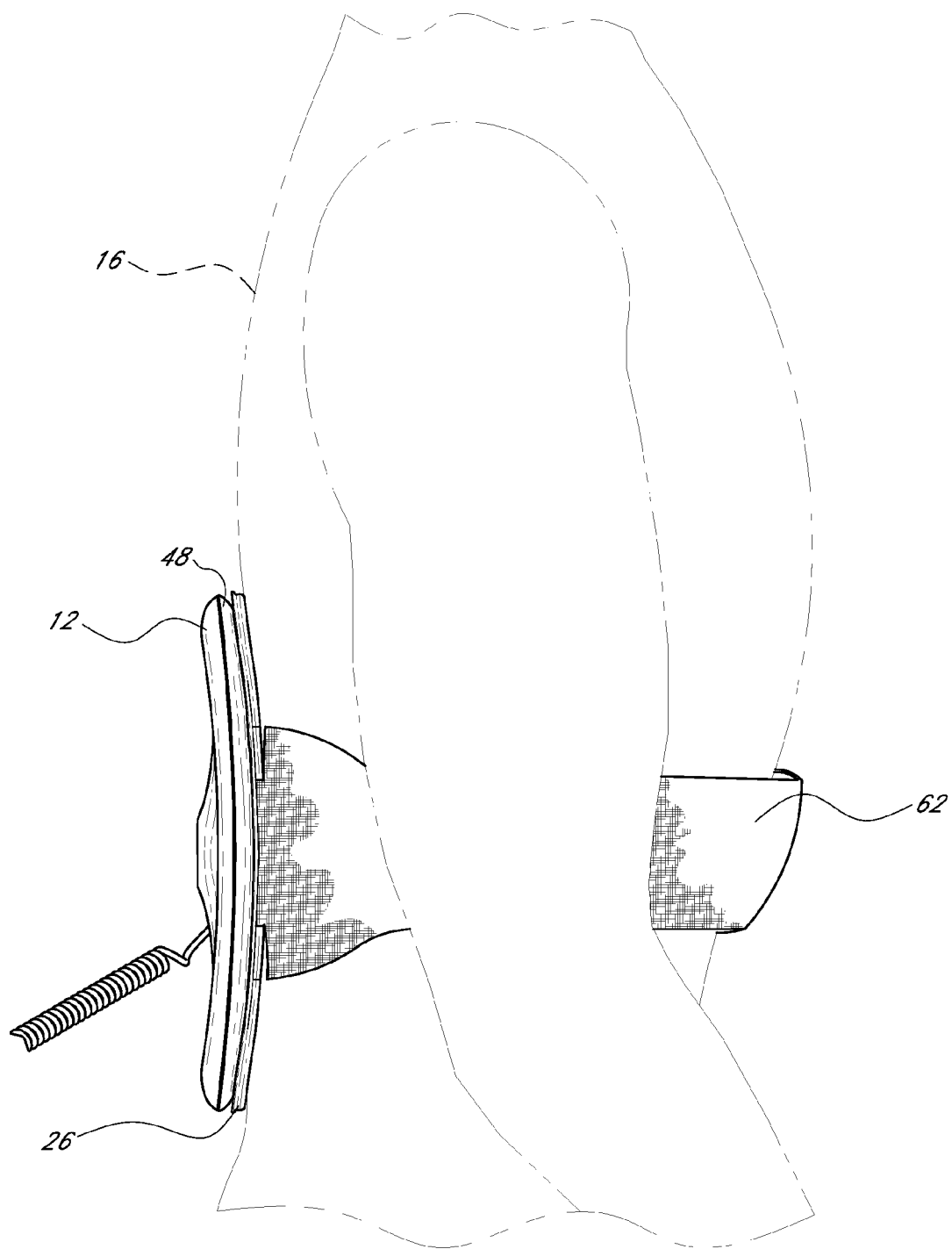
FIG. 2 is a right-side elevational view of the bone growth stimulator of FIG. 1 secured to a wearer's lower back.
Figure 6:
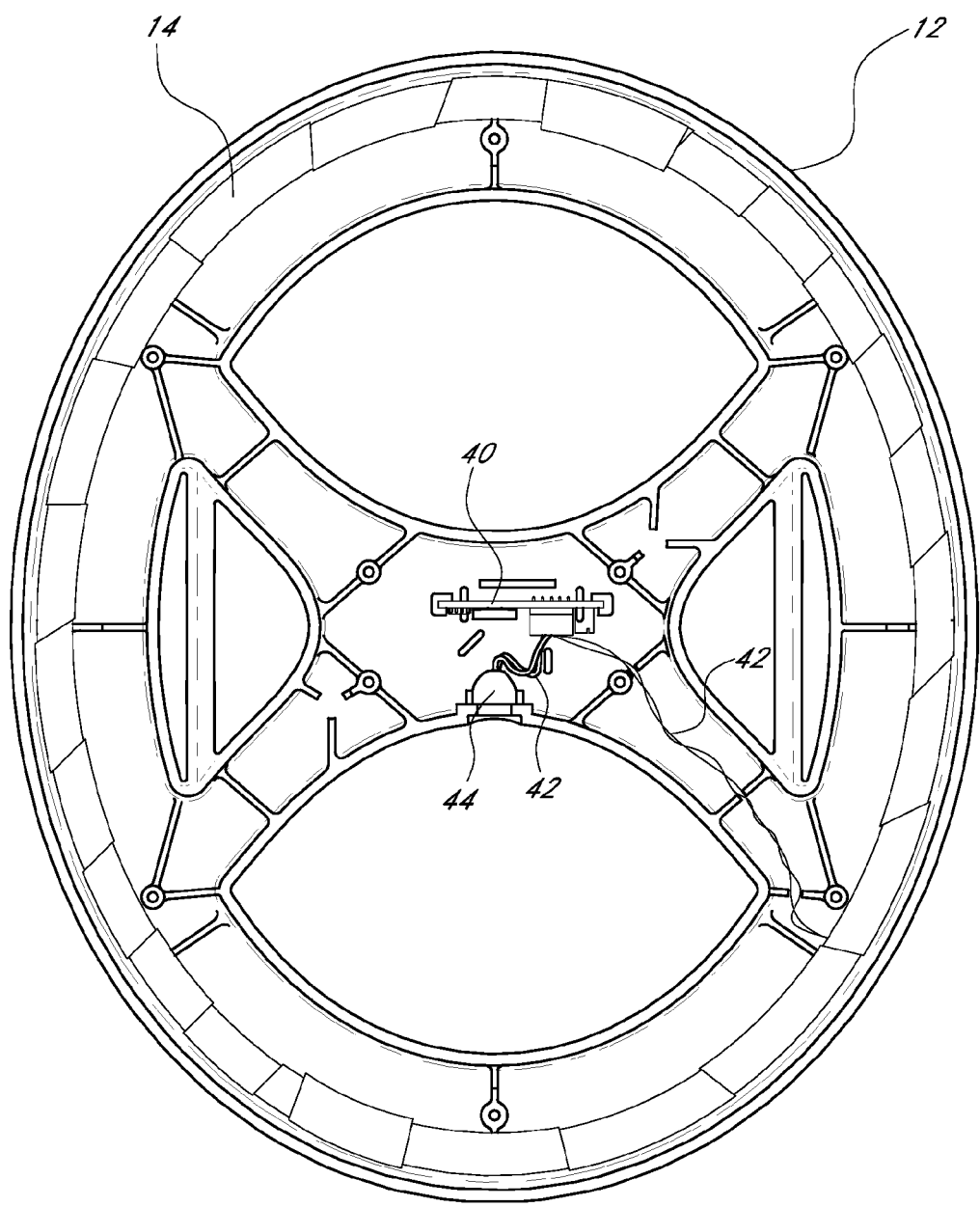
FIG. 6 is a rear elevational view of the housing for the transducer coil of the bone growth stimulator of FIG. 1, illustrating a rear cover of the housing removed to expose the coil.

FIG. 1 illustrates a preferred embodiment of the present bone growth stimulator 10. The device 10 may be used, for example, as an adjunct to spinal fusion, or in other applications where it is beneficial to stimulate the growth of bone cells. The device 10 includes a housing 12 that contains an electrical transducer coil 14 (FIG. 6). The coil 14 comprises a plurality of windings of electrically-conductive wire. When a voltage is applied across the windings, as described below, the coil 14 produces a magnetic field that is useful for stimulating the growth of bone cells. The housing 12 may be placed at the small of the wearer's back 16, as shown in FIG. 2, so that the wearer's spine is positioned within the magnetic field generated by the coil 14. The magnetic field stimulates the growth of bone cells within the spine.

With continued reference to FIG. 1, the device 10 further includes a control box 18 that communicates with the transducer coil 14 via electrical wiring 20. Those of ordinary skill in the art will appreciate that the device may include a control device that communicates with the transducer coil remotely, that is, without any electrical wiring extending between the control device and the transducer coil. The control box 18 preferably contains a power source (not shown), such as batteries, to power the device 10, and a signal generating printed circuit board (not shown). The power source generates a voltage, which is then output to the transducer coil 14. The current traveling through the coil 14 generates a magnetic field around the coil 14, in a manner well-known in the art.

The printed circuit board creates and controls the electrical output to the transducer coil 14. A display panel 22 on the control box 18 provides information to the user about the operating status of the device 10. In the illustrated embodiment, the display panel 22 comprises an LCD display. The control box 18 further comprises a push button 24 for activating and deactivating the device 10. Alternatively, means for controlling the device 10 could be integral with the device 10.

Figure 3:
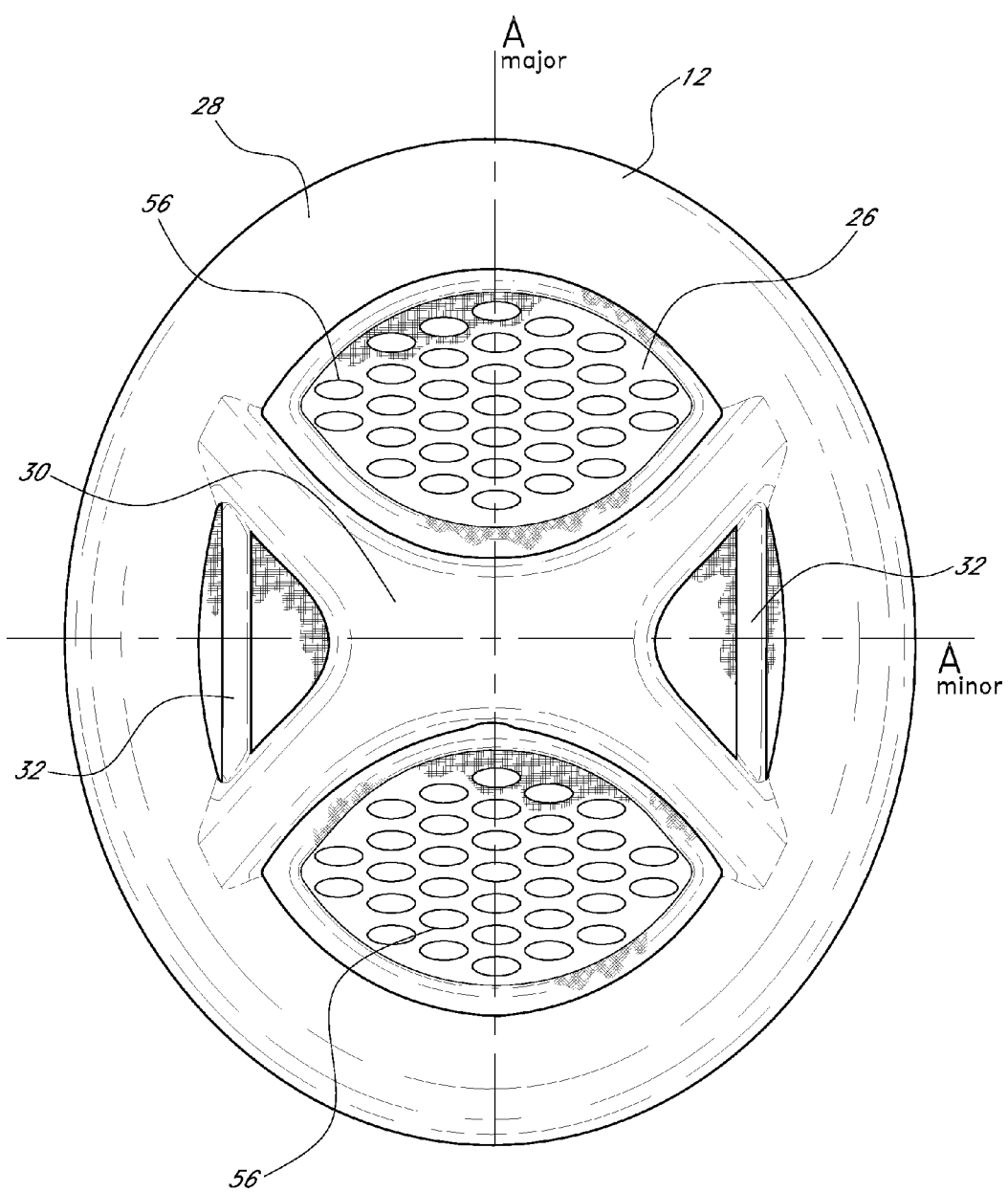
FIG. 3 is a front elevational view of the housing for the transducer coil of the bone growth stimulator of FIG. 1.
Figure 4:
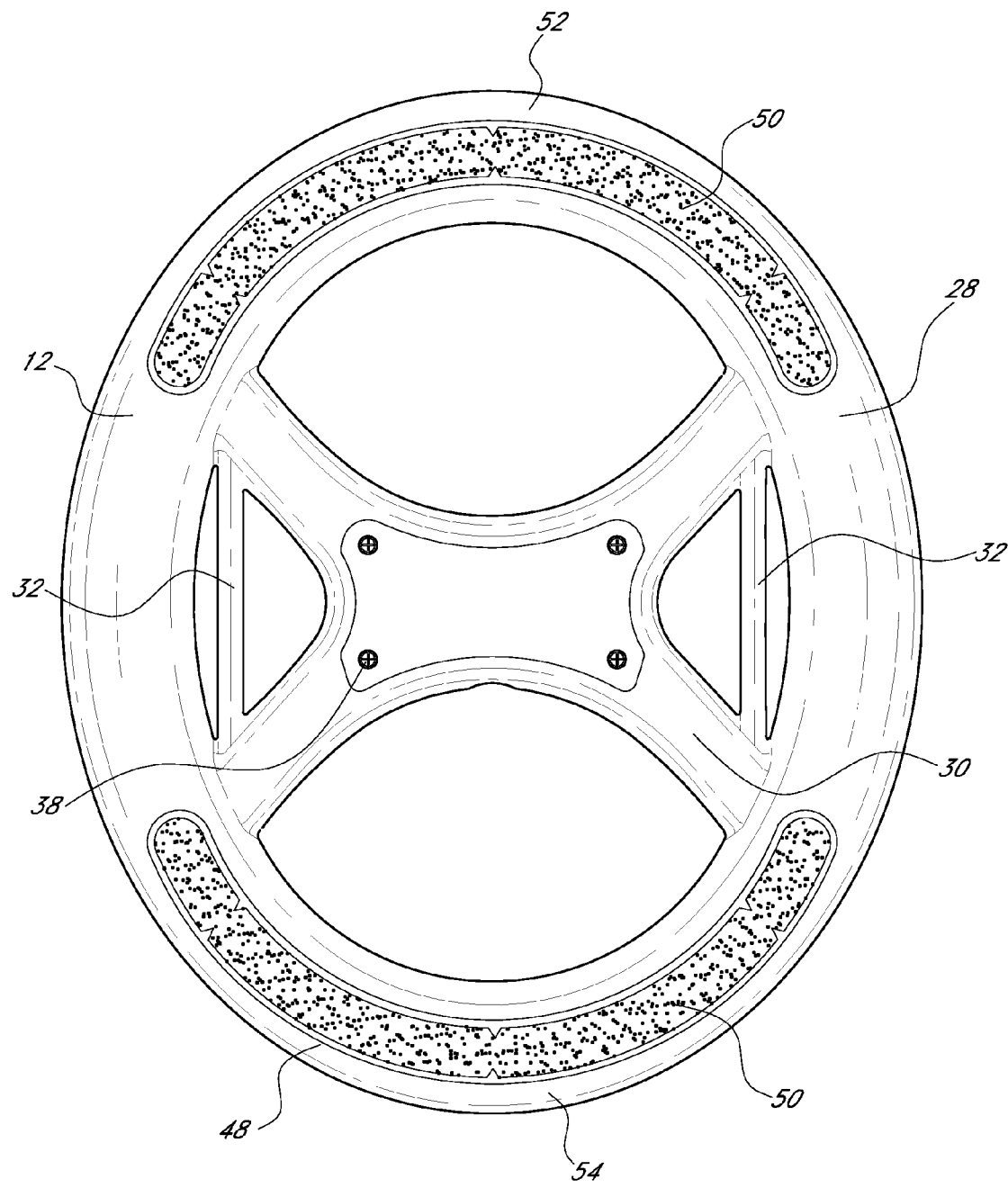
FIG. 4 is a rear elevational view of the housing for the transducer coil of the bone growth stimulator of FIG. 1.

FIGS. 3 and 4 illustrate the housing 12 in front and rear elevational aspect, respectively. In FIG. 3, the housing 12 is illustrated together with a wearer interface pad 26 (see FIG. 5), while in FIG. 4 the pad 26 has been removed for clarity. The housing 12 includes an outer ring portion 28 that is shaped substantially as an ellipse. The elliptical shape of the housing 12 provides support and containment for the coil 14, which also preferably has an elliptical shape (FIG. 6). However, those of ordinary skill in the art will appreciate that the housing 12 and/or the coil 14 could have a different shape, such as circular.

With reference to FIG. 3, the elliptical housing 12 and coil 14 each include a major axis $A_{major}$ and a minor axis $A_{minor}$. With reference to FIG. 2, when the housing 12 is positioned in the wearer's lumbar region and the wearer is standing, the major axis $A_{major}$ extends substantially vertically along the wearer's spine and the minor axis $A_{minor}$ extends substantially horizontally. Those of ordinary skill in the art will appreciate that the housing 12 could be oriented differently when positioned in the wearer's lumbar region. For example, the major axis $A_{major}$ could extend substantially horizontally and the minor axis $A_{minor}$ could extend substantially vertically along the wearer's spine. However, no matter the orientation of the wearer, both the major axis $A_{major}$ and the minor axis $A_{minor}$ are preferably substantially perpendicular to the wearer's anterior/posterior axis when the device 10 is positioned adjacent the wearer's lumbar region.

With further reference to FIGS. 3 and 4, the housing 12 includes a central portion 30 that is shaped substantially as an X. The central portion 30 braces the outer ring portion 28, increasing the structural integrity and durability of the housing 12. The central portion 30 also provides support and containment for additional components of the device 10. Those of ordinary skill in the art will appreciate that the central portion could embody a number of other shapes, such as a three-pointed star or a five-pointed star.

The housing 12 further includes first and second substantially vertical posts 32 disposed on opposite sides of the central portion 30. Each post 32 extends between vertically spaced arms of the X-shaped central portion 30. The posts 32 are adapted to receive end portions of straps that secure the housing 12 to the wearer, as described below. Alternatively, the posts 32 may be eliminated, and the straps may be secured directly to the other portions of the housing 12.

The housing 12 is preferably constructed of a material that is durable and lightweight. In one embodiment, the housing 12 is constructed of a plastic, such as an ABS/PC blend. Those of ordinary skill in the art will appreciate that other materials, such as metals, could be used to construct the housing 12. To reduce manufacturing costs, the housing 12 may be injection-molded. In the illustrated embodiment, the housing 12 is constructed of two pieces (a front piece 34 and a back piece 36, FIG. 1) that are each formed separately and then secured together. For example, the pieces 34, 36 may be secured together with screws 38 (FIG. 4) and/or the pieces 34, 36 may include mating tabs and slots (not shown) that allow the pieces 34, 36 to snap together. The mating pieces 34, 36 define a hollow interior space that contains several components, as described below.

The central portion 30 of the housing 12 includes an interior space that contains electrical circuitry. For example, the circuitry may comprise a printed circuit board 40 that includes a sensor. The sensor may measure the output of the device 10 and feed the information back to the main printed circuit board (in the control box 18) to control the magnetic field output of the device 10. Electrical wiring 42 extends from the printed circuit board to the coil 14, and from the printed circuit board to an input socket 44 that receives a plug 46 (FIG. 1) at one end of the wiring 20 that extends between the control box 18 and the housing 12.

With reference to FIG. 6, the transducer coil 14 preferably extends around the periphery of the space inside the outer ring portion 28 of the housing 12. The coil 14 thus forms an ellipse when viewed in front or rear elevational aspect. In this configuration, the coil 14 produces a magnetic field that stimulates the growth of bone cells in the wearer's spine, thus producing a therapeutic benefit for the wearer.

With reference to FIG. 4, in the illustrated embodiment a rear surface 48 of the housing 12 includes portions of a hook portion 50 of a hook-and-loop fastener. The hook portions are located along an upper end 52 and a lower end 54 of the outer ring portion 28. However, the hook portions 50 could be located in other areas. The hook portions 50 are adapted to receive a wearer interface pad 26, which is illustrated in FIGS. 1-3 and 5. Those of ordinary skill in the art will appreciate that a wearer interface pad could be secured to the housing 12 in another manner, such as with snaps, or the pad could wrap entirely around the housing 12.

In one embodiment, the pad 26 is constructed of a soft, flexible material that is comfortable for wear against the skin. For example, the pad 26 may be constructed of urethane foam. An outer surface of the pad 26 preferably includes a loop portion of a hook-and-loop fastener. In the urethane foam embodiment, substantially the entire outer surface of the pad 26 is covered with loop material. The pad 26 includes a perimeter that is substantially the same size and shape as the outer ring portion 28. The pad 26 is thus adapted to be received upon the rear surface 48 of the housing 12, such that the outer perimeters of the pad 26 and housing 12 substantially align. Abutting contact between the hook portions 50 and the loop material on the pad 26 retains the pad 26 upon the housing 12.

Figure 5:
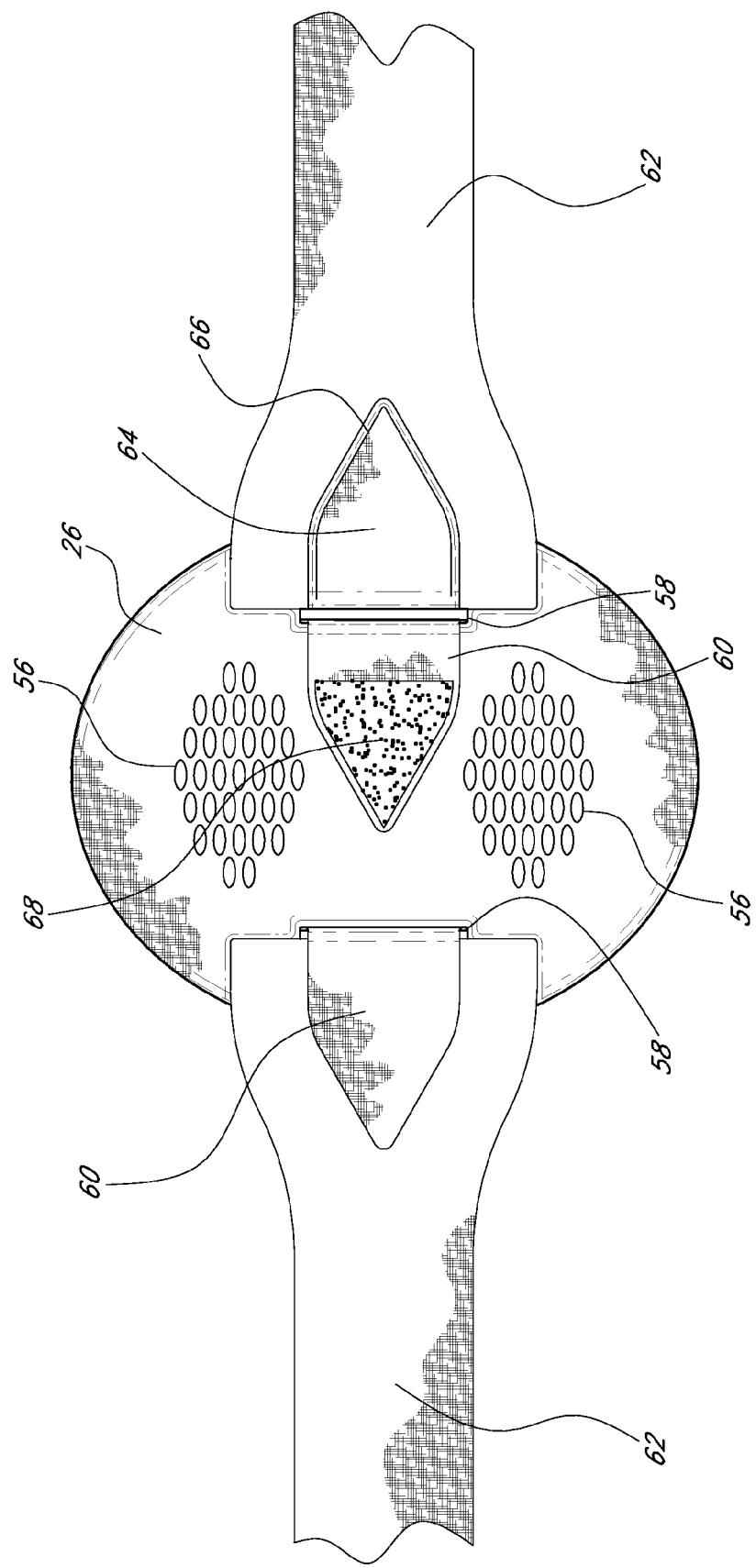
FIG. 5 is a rear elevational view of the bone growth stimulator of FIG. 1.

With reference to FIGS. 3 and 5, in the illustrated embodiment, the pad 26 includes a plurality of holes 56 in upper and lower regions. The holes 56 increase the breathability of the device 10 by enabling heat and moisture from the wearer to pass through the pad 26. However, those of skill in the art will appreciate that the holes 56 need not be provided. The pad 26 further includes first and second substantially vertical slits 58 that align with the posts 32 on the housing 12. The slits 58 enable end portions 60 of straps 62 to pass through, so that the straps 62 can be secured to the housing 12. An end portion 60 of each strap 62 passes through its respective slit 58, around its respective post 32, back through the slit 58, and folds over the strap 62, as shown in FIG. 5. Each strap 62 preferably includes a depressed portion 64 having a perimeter 66 that matches the perimeter shape of the strap end portion 60. The strap end portion 60 thus nests within the depression 64. In one embodiment, the strap end portion 60 includes a portion of a hook portion 68 of a hook-and-loop fastener. The hook portion 68 mates with loop material in the depression 64 to secure the strap end portion 60 to the strap 62.

As illustrated in FIG. 2, the housing 12 and pad 26 rest against the wearer's lower back when the device 10 is in use. The pad 26 directly abuts the wearer (although the wearer may wear the device 10 over his or her clothing) and provides a comfortable interface between the housing 12 and the wearer's skin. The straps 62 extend around the wearer's waist and join at the wearer's abdomen. In one embodiment, an end of one strap 62 includes a hook portion (not shown) of a hook-and-loop fastener, and an end of the other strap 62 includes a loop portion (not shown) of a hook-and-loop fastener. The mating hook-and-loop portions secure the device 10 to the wearer. Those of ordinary skill in the art will appreciate that the ends of the straps 62 could include alternative securing means, such as a buckle, for example. The straps 62 are preferably flexible and soft, so as to be comfortable. In one embodiment, the straps 62 are constructed of the same material as the pad 26.

As FIG. 2 illustrates, the housing 12 includes a curvature so that the rear surface 48 of the housing 12 is convex. The rear surface 48 faces the wearer's lower back when the device 10 is in use. The housing 12 is thus adapted to abut, and nest within, the wearer's lower back, which includes a naturally concave curvature when viewed in profile. The pad 26, which is preferably constructed of a soft and flexible material, conforms to the space between the housing 12 and the wearer's lower back. The curvature of the housing 12 creates a wearer interface that more closely matches the wearer's anatomy and leads to greater wearer comfort. In the illustrated embodiment, the curvature of the housing 12 follows a path that traces an arc of substantially constant radius. However, as those of ordinary skill in the art will appreciate, the curvature of the housing 12 may follow a path that traces an arc of varying radius.

In general, the stronger the magnetic field that can be applied to a treatment area, the greater the therapeutic benefits. Further, the magnetic field generated by a transducer coil has the greatest strength in the area close to the coil. Thus, the curvature of the housing 12 advantageously brings a greater portion of the transducer coil 14 closer to the wearer.

As FIG. 2 illustrates, the curvature of the housing 12 follows the contour of the wearer's back so that there are no gaps between the interface pad 26 and the wearer's skin. Bringing all portions of the coil 14 closer to the wearer brings a stronger portion of the magnetic field closer to the treatment area and creates therapeutic benefits.

SCOPE OF THE INVENTION

The above presents a description of the best mode contemplated for carrying out the present bone growth stimulator, and of the manner and process of making and using it, in such full, clear, concise, and exact terms as to enable any person skilled in the art to which it pertains to make and use this bone growth stimulator. This bone growth stimulator is, however, susceptible to modifications and alternate constructions from that discussed above that are fully equivalent. Consequently, this bone growth stimulator is not limited to the particular embodiments disclosed. On the contrary, this bone growth stimulator covers all modifications and alternate constructions coming within the spirit and scope of the bone growth stimulator as generally expressed by the following claims, which particularly point out and distinctly claim the subject matter of the bone growth stimulator.

What is claimed is:

1. A device for stimulating bone growth, comprising:
   a transducer coil for generating a stimulating magnetic field;
   a substantially rigid housing configured to support and contain the transducer coil, wherein the housing includes a first surface having a convex curvature that curves around a first axis, the first surface configured to be positioned on a wearer over a location on the wearer's back to deliver the magnetic field to that location;
   a strap extending from the housing substantially parallel to the first axis; and
   a pad constructed of a relatively soft and flexible material and configured to be secured to the first surface of the housing, wherein the pad comprises first and second slits, and the strap passes through the first or second slit.

2. The device for stimulating bone growth of claim 1, wherein a second surface of the housing opposite the first surface is concave.

3. The device for stimulating bone growth of claim 1, wherein the housing includes an outer ring portion that is shaped substantially as an ellipse.

4. The device for stimulating bone growth of claim 3, wherein the housing further includes a central portion that is disposed within a region defined by the outer ring portion and is spaced away from the outer ring portion.

5. The device for stimulating bone growth of claim 4, wherein the region defined by the outer ring portion comprises a plurality of arms configured substantially as an X.

6. The device for stimulating bone growth of claim 1, further comprising a control box configured to control input to and output from the transducer coil.

7. The device for stimulating bone growth of claim 1, wherein the housing traces an arc of substantially constant radius.

8. The device for stimulating bone growth of claim 1, wherein the transducer coil has an elliptical shape.

9. The device for stimulating bone growth of claim 3 wherein the housing is configured to be positioned on the wearer over the location on the wearer's back such that a major axis and a minor axis of the housing are substantially perpendicular to an anterior/posterior axis of the wearer.

10. The device for stimulating bone growth of claim 1, wherein the pad includes a plurality of holes extending through the pad.

11. The device for stimulating bone growth of claim 3, further comprising:
   elongate posts disposed within a region defined by the outer ring portion, wherein the elongate posts are aligned substantially perpendicular to the first axis.

12. The device for stimulating bone growth of claim 1, further comprising a second strap, wherein the two straps extend from substantially opposite sides of the housing.

* * * * *